United States Patent [19]

McGregor et al.

[11] Patent Number: 4,824,996
[45] Date of Patent: Apr. 25, 1989

[54] PHOSPHOLIPASE A2 INHIBITORS

[75] Inventors: William H. McGregor, Malvern; Joseph Y. Chang, Berwyn, both of Pa.

[73] Assignee: American Home Products Corporation, New York, N.Y.

[21] Appl. No.: 927,907

[22] Filed: Nov. 6, 1986

Related U.S. Application Data

[63] Continuation-in-part of Ser. No. 895,762, Aug. 12, 1986, abandoned.

[51] Int. Cl.$^4$ ............................................. C07C 127/15
[52] U.S. Cl. ..................................... 560/165; 544/386; 564/58; 564/59; 564/81; 564/98; 564/151; 564/197; 260/404.5
[58] Field of Search ....................... 564/58, 59, 81, 98, 564/151, 197; 560/165; 260/404.5 H, 404.5 PH

[56] References Cited

U.S. PATENT DOCUMENTS

| | | | |
|---|---|---|---|
| 2,970,159 | 1/1961 | Gutmann et al. | 260/404.5 H |
| 3,598,871 | 8/1971 | Kraebel | 564/35 |
| 3,715,326 | 2/1973 | Traubel et al. | 521/217 |
| 3,850,969 | 11/1974 | Grimm et al. | 260/404.5 |
| 3,965,015 | 6/1976 | Bauman | 252/8.8 |
| 4,148,659 | 4/1979 | Yuyts et al. | 96/48 HD |
| 4,218,465 | 8/1980 | Grange et al. | 514/562 |
| 4,326,067 | 4/1982 | Fazio | 260/404.5 PA |

FOREIGN PATENT DOCUMENTS

| | | |
|---|---|---|
| 108390 | 9/1974 | Fed. Rep. of Germany . |
| 1594238 | 7/1981 | United Kingdom . |

OTHER PUBLICATIONS

Wang, "Applied Spectroscopy," vol. 22, No. 3, 1968, pp. 167-169.
Vogt, "Advances in Prostaglandin and Thromboxane Research," vol. 3, 1978, pp. 89-95.
Gryglewski, "CRC Crital Reviews in Biochem.", 1986, pp. 291-338.
Bryan, "Amer. Journ. of Path.", vol. 99, No. 3, 1980, pp. 743-766.
Bach et al., "Journ. Immun.", vol. 125(1), 1980, pp. 115-117.
Bach et al., "Biochem and Biophy. Res. Commun.", vol. 93 (4), 1980, pp. 1121-1126.
Dahlen et al., "Nature", vol. 288(4), 1980, pp. 484, 486.
Hutchinson, "J. Royal Soc. Med.", vol. 74, 1981, pp. 831-833.
"Chemical Abstracts", vol. 71, 1968, Col. 31025q.
Wang, "Chemical Abstracts", vol. 69, 1968, Col. 14270z.
Furdik et al., "Chemical Abstracts", vol. 67, 1967, Col. 116858y.
Hunter, "Chemical Abstracts", vol. 78, 192, Col. 110903q.
Ikeda et al., "Chemical Abstracts", vol. 83, 1975, Col. 9057v.
Yuyts et al., "Chemical Abstracts", vol. 90, 1978, Col. 64523p.
Kramer et al., "Chemical Abstracts", vol. 96, 1981, Col. 92631q.
Bailey et al., "Ann. Report Med. Chem.", vol. 17, 1982, pp. 203-217.
Flower et al., "Nature", vol. 278, 1979, pp. 456-459.
Hirata et al., "Proc. Natl. Acad. Sci. U.S.A.", vol. 77, 1980, pp. 2533-2536.
Bills et al., "Biochimica Biophysica Acta", vol. 424, 1976, pp. 303-314.
Pickett et al., "Biochem. J.", 1976, vol. 160, pp. 405-408.
Giebler et al., "Pharm. Res. Commun.", vol. 9, No. 2, 1977, pp. 117-130.
Keil et al., "Chemical Abstracts", vol. 90, 1979, Col. 90:105,526n.

Primary Examiner—Richard L. Raymond
Assistant Examiner—James H. Turnipseed
Attorney, Agent, or Firm—George Tarnowski

[57] ABSTRACT

There are disclosed compounds of the formula $$R^1\text{-}X$$

wherein
$R^1$ is alkyl of 8-22 carbon atoms;
X is

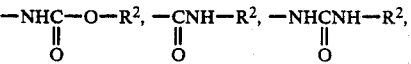

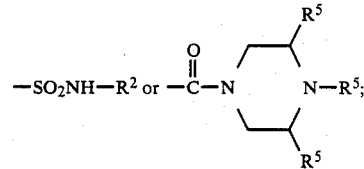

$R^2$ is $-(CH_2)_n NR^4R^5$;
$R^3$ is hydrogen or lower alkyl;
$R^4$ is hydrogen or lower alkyl;
$R^5$ is hydrogen or lower alkyl; and
n is 0-7, with the proviso that when X is

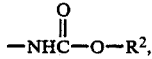

n is 6-7; and their use in the prevention and/or treatment of conditions such as allergic rhinitis, allergic bronchial asthma and other naso-bronchial obstructive air-passageway conditions, other immediate hypersensitivity reactions such as allergic conjunctivitis and various inflammatory conditions.

4 Claims, No Drawings

PHOSPHOLIPASE A2 INHIBITORS

This is a continuation-in-part of U.S. Ser. No. 895,762, filed Aug. 12, 1986, now abandoned.

The present invention is directed to a series of substituted N,N-dialkylaminoalkyl carbamates having anti-inflammatory activity.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980).

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophys. Res. Commun.* 93, 1121–1126 (1980)].

The signficance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

It is now generally accepted that the release of free arachidonic acid from membrane phospholipids by the enzyme phospholipase $A_2$ ($PLA_2$) is the critical first step in the initiation of the synthesis of the various eicosanoids arising from the cyclooxygenase and lipoxygenase pathways. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci. U.S.A.*, 77, 2533 (1980)]. $PLA_2$ catalyzes the specific hydrolysis of the fatty-acid ester linkage at the 2-position of 1,2-diacyl-sn-phosphoglycerides and two major pathways for the $PLA_2$-mediated arachidonic acid release have been proposed to account for phospholipid hydrolysis. According to the first, the $PLA_2$-mediated cleavage of AA from the 2-position of phosphatidylcholine and phosphatidylethanolamine occurs during platelet activation [Bills et al., *Biochem. Biophys. Acta*, 424, 303 (1979)], while according to the second, phosphatidylinositol, which turns over very rapidly, may also serve as the initial source of AA.

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the prostaglandins, thromboxanes and leukotrienes. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt. *Adv. Prostagl. Thromb. Res.*, 3, 89 (1978)], the inhibition of $PLA_2$ is indicated in the therapeutic treatment of cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compounds of the formula $$R^1\text{-}X$$

wherein
$R^1$ is alkyl of 8–22 carbon atoms;
X is

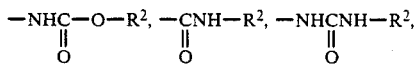

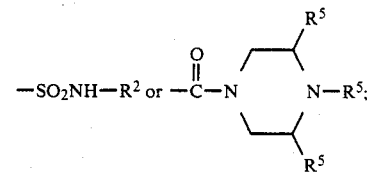

$R^2$ is $-(CH_2)_n NR^4R^5$;
$R^4$ is hydrogen or lower alkyl;
$R^5$ is hydrogen or lower alkyl; and
n is 0–7, with the proviso that when X is

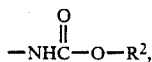

n is 6–7.

The term "lower alkyl" refers to moieties having 1–6 carbon atoms in the carbon chain.

The compounds of the invention can be prepared by the following reaction schemes. The compounds of the formula $$R^1-NH\overset{O}{\underset{\|}{C}}-OR^2$$

can be prepared by reacting the appropriate alkyl isocyanate with an aminoalkanol:

$$R^1N=C=O + R^2OH \longrightarrow R^1NH-\overset{O}{\underset{\|}{C}}-OR^2$$

The reaction is preferably carried out in an organic solvent, such as tetrahydrofuran. In like manner, when it is desired to obtain compounds having the formula $$R^1-NH\overset{O}{\underset{\|}{C}}-NH-R^2$$

an appropriate alkyl isocyanate is reacted with an aminoalkylamine:

$$R^1-N=C=O + NH_2R^2 \longrightarrow R^1NH\overset{O}{\underset{\|}{C}}-NHR^2$$

Again, the reaction is carried out in an organic solvent, preferably tetrahydrofuran.

Compounds of the invention having the formula $$R^1-\overset{O}{\underset{\|}{C}}NH-R^2$$

can be prepared by reacting the appropriate carboxylic acid with carbonyl diimidazole in an organic solvent, followed by reacting the intermediate obtained thereby with an appropriate aminoalkylamine:

$$R^1COOH + N\diagup\!\!\!\diagdown N-\overset{O}{\underset{\|}{C}}-N\diagup\!\!\!\diagdown N \longrightarrow$$

$$R^1-\overset{O}{\underset{\|}{C}}-N\diagup\!\!\!\diagdown N \xrightarrow{R^2NH_2} R^1-\overset{O}{\underset{\|}{C}}NH-R^2$$

Where the compounds of the invention have the formula $$R^1-\overset{O}{\underset{\|}{C}}NH-(CH_2)_nNR^4R^5$$

and n=0, the reaction scheme just outlined is modified in the last step, where the reactant used is an appropriate hydrazine instead of an aminoalkylamine:

$$R^1-\overset{O}{\underset{\|}{C}}-N\diagup\!\!\!\diagdown N \xrightarrow{NH_2NR^4R^5} R^1-\overset{O}{\underset{\|}{C}}N-NR^4R^5.$$

This same reaction scheme can again be varied to produce compounds of the invention having the formula $$R^1-\overset{O}{\underset{\|}{C}}-N\diagup\diagdown_{R^5}^{R^5}N-R^5$$

whereby the acyl imidazole intermediate is reacted with the appropriate piperazine:

$$R^1-\overset{O}{\underset{\|}{C}}-N\diagup\!\!\!\diagdown N + HN\diagup\diagdown_{R^5}^{R^5}N-R^5 \longrightarrow$$

$$R^1-\overset{O}{\underset{\|}{C}}-N\diagup\diagdown_{R^5}^{R^5}N-R^5$$

Finally, compounds of the invention having the formula $$R^1-SO_2NH-R^2$$

can be prepared by reacting the appropriate alkylsulfonyl halide with an aminoalkylamine in an organic solvent, preferably tetrahydrofuran:

$$R^1-SO_2Cl + R^2NH_2 \rightarrow R^1-SO_2NH-R^2$$

All of the starting compounds used in the preparation of the compounds of the invention are commercially available or can be readily prepared by conventional procedures taught in the chemical literature.

The compounds of the invention, by virtue of their ability to inhibit activity of $PLA_2$ enzyme, are useful in the treatment of conditions indicated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis and the like.

When the compounds of the invention are employed in the treatment of allergic airways disorders or an anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed.

The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the example given hereafter, illustrate the ability of the compounds of the invention to inhibit the activity of $PLA_2$ enzyme in vitro; and measures the in vivo activity of the compounds as anti-inflammatory agents in the murine assay.

EXAMPLE 1

Dodecylcarbamic acid 6-(dimethylamino)hexyl ester 1.1 gm (5 meq) of dodecyl isocyanate and 726 mg (5 meq) of 6-(dimethylamino)hexanol are combined in 5 ml of tetrahydrofuran and reacted over weekend at room temperature. The insoluble crystals are filtered, washed with ethyl acetate and the filtrate and washings combined, evaporated under reduced pressure (<30° C.) and dried in vacuo. The product is purified by silica gel chromatography in the system $CH_2Cl_2:CH_3OH:NH_4OH$ (65:25:4). Fractions 34-46 are combined, evaporated and dried in vacuo to yield 300 mg ($R_f$ 0.9 S.G. $CH_2Cl_2$, $CH_3OH$, $NH_4OH$) of title compound.

Analysis for: $C_{21}H_{44}N_2O_2$: Calculated: C, 70.73; H, 12.44; N, 7.86. Found: C, 70.72; H, 12.66; N, 8.00.

IR KBr 1300, 1460, 1525, 1708, 2830, 2915.

EXAMPLE 2

Hexadecylcarbamic acid 6-(dimethylamino)hexyl ester 1.34 gm (5 meq) of hexadecyl isocyanate and 726 mg (5 meq) of 6-(dimethylamino)hexanol are combined in 5 ml of tetrahydrofuran and reacted over weekend at ambient temperature. The crystalline insoluble is removed by filtration and the filtrate evaporated under reduced pressure (<30° C.) and dried in vacuo. The product is purified by silica gel chromatography in the system $CH_2Cl_2:CH_3OH:NH_4OH$ (65:25:4). Fractions 43-53 are combined ($R_f$ 0.9 TLC S.G. $CH_2Cl_2$, $CH_3OH$, $NH_4OH$), m.p. 50°-52° C., softens at 46° C.

Analysis for: $C_{25}H_{52}N_2O_2$: Calculated: C, 73.18; H, 12.76; N, 6.57. Found: C, 72.16; H, 13.02; N, 6.63.

IR, KBr 1760, 2840, 2910, 3340.

EXAMPLE 3

Hexadecylcarbamic acid 3-(dimethylamino)propyl ester 1.34 gm (5 meq) of hexadecyl isocyanate and 515 mg (5 meq) of 3-(dimethylamino)propanol are combined in 5 ml of tetrahydrofuran and reacted overnight at room temperature. The insoluble crystals are filtered, washed on the filter with ethyl acetate and the filtrate and washings evaporated under reduced pressure (<30° C.) and dried in vacuo. The product is purified by silica gel chromatography in the system $CH_2Cl_2:CH_3OH:NH_4OH$ (65:25:4). Fractions 48-60 are combined, evaporated under reduced pressure <30° C. and dried in vacuo to yield 215 mg ($R_f$ 0.9 TLC S.G. $CH_2Cl_2$, $CH_3OH$, $NH_4OH$), of title compound.

Analysis for: $C_{22}H_{46}N_2O_2$: Calculated: C, 71.30; H, 12.51; N, 7.56. Found: C, 71.46; H, 12.65; N, 7.40.

IR KBr 1250, 1465, 1525, 1687, 2850, 2910, 3350.

EXAMPLE 4

N-[3-(dimethylamino)propyl]pentadecanamide 1.37 gm (6 meq) of myristic acid and 972 mg (6 meq) of carbonyl diimidazole are combined in a minimum volume of tetrahydrofuran and reacted at room temperature for 1 hour. 0.8 Ml (6 meq+10%) of 3-dimethylaminopropylamine is added and reacted overnight at room temperature. The reaction mixture is evaporated under reduced pressure, dried in vacuo and the desired product purified by silica gel chromatography in the system $CH_2Cl_2:CH_3OH:NH_4OH$ (65:25:4). Fractions 53-65 are combined, evaporated and dried in vacuo to yield 325 mg of title compound having a m.p. of 46°-48° C. after recrystallization from acetone/water.

Analysis for: $C_{20}H_{42}N_2O$: Calculated: C, 73.56; H, 12.96; N, 8.58. Found: C, 72.11; H, 13.22; N, 8.86.

IR KBr 1635, 2850, 2920, 3310.

EXAMPLE 5

Hexylcarbamic acid 6-(dimethylamino)hexyl ester 0.65 ml (5 meq) of hexyl isocyanate and 726 mg (5 meq) 6-(dimethylamino)hexanol are combined in 5 ml of tetrahydrofuran and reacted over a weekend at room temperature. The reaction mixture is evaporated under reduced pressure (<30° C.), dried in vacuo and the product purified by silica gel chromatography in the system $CH_2Cl_2:CH_3OH:NH_3$ (65:25:4). Fractions 50-64 are combined, evaporated under reduced pressure <30° C. and dried in vacuo to yield 460 mg of title compound.

Analysis for: $C_{15}H_{32}N_2O_2$: Calculated: C, 66.13; H, 11.84; N, 10.28. Found: C, 66.01; H, 11.76; N, 10.22.

IR KBr 1250, 1705, 1730(S), 2930, 3330.

EXAMPLE 6

N-[3-(dimethylamino)propyl]-N'-hexadecylurea 1.34 ml (5 meq) of hexadecyl isocyanate and 0.7 ml (5 meq) of 3-dimethylaminopropylamine are combined in 5 ml of tetrahydrofuran and reacted over a weekend at room temperature. The reaction mixture is filtered, washed with tetrahydrofuran, dried in vacuo and recrystallized from acetone to yield 1.2 gm of title compound with a m.p. of 78°-79° C.

Analysis for: $C_{22}H_{47}N_3O$: Calculated: C, 71.48; H, 12.82; N, 11.37. Found: C, 71.67; H, 12.79; N, 11.26.

EXAMPLE 7

N-[7-(dimethylamino)heptyl]-1-hexadecanesulfonamide 650 mg (2 meq) of hexadecanesulfonylchloride are added dropwise to 744 mg (4 meq) of 7-dimethylaminoheptylamine stirring in tetrahydrofuran at 0° C. The reaction mixture is evaporated under reduced pressure (<30° C.) dried in vacuo, and chromatographed on silica gel in the system $CH_2Cl_2:CH_3OH:NH_4OH$ (65:25:4) and fractions 47–52 having $R_f$ 0.9 on TLC S.G. $CH_2Cl_2:CH_3OH:NH_4OH$ are combined, evaporated under reduced pressure <30° C. and dried in vacuo to yield 300 mg of title compound having a m.p. of 56°–57.5° C. uncorr.

Analysis for: $C_{27}H_{58}N_2O_2S$: Calculated: C, 68.40; H, 12.20; N, 5.91. Found: C, 68.54; H, 12.20; N, 5.86.

IR, KBr 1460, 2850, 2910.

NMR 0.9 (t, 9H—$CH_3$), 1.25 (S, 40H—$CH_2$), 2.5 (m, 6H—$CH_2$—N—), 2.94 (m, 2H—$CH_2$—$SO_2NH$).

EXAMPLE 8

Tetradecanoic acid 2,2-dimethylhydrazide 690 mg (3 meq) of myristic acid and 486 mg (3 meq) of carbonyl diimidazole are reacted in a minimum volume of tetrahydrofuran at room temperature for 1 hour. Unsym-dimethylhydrazine (0.23 ml, 3 meq) is added and reacted overnight at room temperature. The reaction mixture is evaporated under reduced pressure, dried in vacuo and purified on a silica gel column using $CH_2Cl_2:CH_3OH$ (5:1). The fractions having $R_6$ 0.76 on TLC S.G. $CH_2Cl_2:CH_3OH$ (5:1) chlorine-peptide spray are combined, evaporated under reduced pressure and dried in vacuo to yield 185 mg of title compound having a m.p. of 63.5°–64.5° C.

Analysis for: $C_{16}H_{34}N_2O$: Calculated: C, 71.05; H, 12.67; N, 10.36. Found: C, 70.94; H, 12.66; N, 10.29.

IR 1640, 2840, 2900.

NMR 0.92 (t, 3H—$CH_3$), 1.32 (S, 10H—$CH_2$), 2.1 (t, 2H—$CH_2CO$—), 2.54 (S, 6H—$(CH_3)_2$—N).

EXAMPLE 9

3,5-Dimethyl-1-(1-oxotetradecyl)piperazine 685 mg (3 meq) of myristic acid and 486 mg (3 meq) of carbonyl diimidazole are reacted as described in Example 8 and purified on a column of silica gel in the system $CH_2Cl_2:CH_3OH:NH_3$ (65:25:4). The fractions having $R_f$ 0.93 TLC S.S. $CH_2Cl_2:CH_3OH:NH_3$ and $R_f$ 0.74 TLC S.S. $CH_2Cl_2:CH_3OH$ (1:1) using iodine detection are combined, evaporated under reduced pressure and dried in vacuo at ambient temperature.

Analysis for: $C_{20}H_{40}N_2O$: Calculated: C, 74.01; H, 12.42; N, 8.63. Found: C, 72.41; H, 12.34; N, 8.19.

IR film 2930, 1640, 1450.

NMR 0.85 (t, 3H—$CH_3$), 1.1 (d, 6H—$CH_3$), 1.25 (S, 22H—$CH_2$), 2.25 (q, 2H—$CH_2$—CON), 3.6.

$$\begin{matrix} -CH_2 \\ \diagdown \\ (m, 4H \quad N), 4.5(d, 2H-CH-NH-) \\ \diagup \\ -CH_2 \end{matrix}$$

EXAMPLE 10

4-Methyl-1-(1-oxotetradecyl)piperazine 680 mg (3 meq) of myristic acid and 486 mg (3 meq) of carbonyl diimidazole are reacted in a minimum volume of tetrahydrofuran at ambient temperature for 1.5 hours. 1-Methyl-piperazine (0.33 ml, 3 meq) is added and reacted overnight at ambient temperature. The reaction mixture is evaporated under reduced pressure, dried in vacuo and purified on a column of silica gel in the system $CH_2Cl_2:CH_3OH$ (5:1). The fractions having $R_f$ 0.80 on TLC silica gel $CH_2Cl_2:CH_3OH$ (5:1)-iodine are combined, evaporated under reduced pressure (<30°) and dried in vacuo to yield 85 mg of title compound.

Analysis for: $C_{19}H_{39}N_2O$: Calculated: C, 73.49; H, 12.34; N, 9.02. Found: C, 73.23; H, 12.00; N, 9.14.

IR KBr 2900, 1650, 1450, 1300 $cm^{-1}$.

NMR 0.9 (t, 3H—$CH_3$), 1.25 (S, 22H—$CH_2$), 1.6 (t, 3H, N—$CH_3$) 2.25 (q, 2H $CH_2$—CON).

$$\begin{matrix} -CH_2 \\ \diagdown \\ 3.6(m, 4H \quad N) \\ \diagup \\ -CH_2 \end{matrix}$$

EXAMPLE 11

The ability of the compounds to inhibit the activity of $PLA_2$ enzyme is measured in the following in vitro assay.

The assay is carried out as follows:

Substrate Preparation

*E. coli,* cultured to exponential growth, are sedimented for 15 minutes at 10,000 g and resuspended in sterile isotonic saline (1–3 ml). 10–25 $\mu$Ci [1-$^{14}$C] oleic acid is added to a sterile flask, evaporated by $N_2$ and resolubilized with 0.3 ml 20% fatty acid-free BSA. 75–100 ml of nutrient broth and 1 ml *E. coli* are then added to each flask and incubated for 2–3 hours at 37° C. [1-$^{14}$C] oleic acid labelled *E. coli* are then sedimented, suspended in saline and added to fresh nutrient broth and incubated for 1.5 hours at 37° C. to complete [1-$^{14}$C] oleic acid incorporation into the phospholipids. After overnight refrigeration of cultures, *E. coli* are again sedimented, suspended in saline and autoclaved for 15 minutes at 120° C. *E. coli* cultures are washed twice with saline (first wash contains 1% BSA) and resuspended in saline. Non-labelled *E. coli* cultures are also prepared in the same manner. Cell number is determined by measuring the optical density at 550 nm ($3 \times 10$ cell/ml=1 O.D.). The amount of radioactivity associated with cells is determined by counting a defined volume of cell suspension. The specific activity is subsequently adjusted by adding non-labelled *E. coli* to yield $2-4 \times 10$ cpm per $1 \times 10^{10}$ *E. coli.* [1-$^{14}$C] arachidonic acid-labelled *E. coli* are similarly prepared.

Platelet $PLA_2$ Preparation

Expired human platelets from the blood bank are centrifuged for 15 minutes at 200 g to obtain a platelet rich plasma fraction and to remove the red blood cells. Platelets are sedimented for 15 minutes at 2500 g and the plasma is removed before adding cold 0.18N $HSO_4$ (4 ml/unit). Platelets are homogenized, incubated for 1 hour at 4° C., homogenized again and centrifuged for 15 minutes at 10,000 g. The $PLA_2$ enriched supernatant fluid is removed and the amount of protein is determined by the Lowry method. The preparation is divided into various portions and stored at $-20°$ C.

Assay of $PLA_2$ Activity

The assay measures the hydrolysis of E. coli membrane phospholipids and the release of free [1-$^{14}$C] oleic acid from the C-2 position of phospholipids by human platelet PLA$_2$. To ice cold 15×100 mm test tubes, the following additions are made: 2,5×10 E. coli (equivalent to 4 nmol phospholipid), 5 mM Ca$^{++}$, 100 mM Tris buffer (pH=7.4), 100 μg platelet extract (or an amount to produce 20-30% hydrolysis), drug or vehicle. The final volume is adjusted to 500 μl with water. Mixtures are vortexed and incubated for 30 minutes in a shaking water bath. It should be noted that preliminary experiments are always performed with each new batch of platelets to establish linear hydrolysis of phospholipids with regard to protein concentration and time. The enzyme reaction is stopped by the addition of 3 volumes of CHCl$_3$ to each tube which is vortexed and then centrifuged for 5 minutes at 500 g. The lower CHCl$_3$/CH$_3$OH phase is removed and evaporated under N. The dried residue is redissolved in 50 μl CHCl$_3$:CH$_3$OH (9:1 v/v), spotted on aluminum-backed chromatographic plates and developed in a solvent system consisting of petroleum ether:diethyl ether:acetic acid (80:20:1). Free fatty acid ([1-$^{14}$C]oleic acid) and [1-$^{14}$C]oleic acid labeled phospholipids are visualized with exposure to iodine vapors. Radioactive areas that cochromatographed with authentic oleic acid and phospholipid standards are cut out and placed in a scintillation vial. One ml CH$_3$OH and 10 ml Hydrofluor are added to each cut strip and radioactivity is determined by liquid scintillation counting.

The percent hydrolysis is calculated by the following equation:

$$\% \text{ Hydrolysis} = \frac{\text{free fatty acid (dpm)}}{\text{total phospholipid + free fatty acid (dpm)}}$$

Rate of Hydrolysis (nmol/min) =

$$\frac{\% \text{ hydrolysis} \times \text{total phospholipid content (5 nmol)}}{\text{incubation time (min)}}$$

Activity of standard drugs:

| Drug | Inhibition of PLA$_2$ Activity IC$_{50}$, μM |
|---|---|
| Indomethacin | 48 |
| Gold Sodium Thiomalate | 43 |

When tested in the above-described assay, the compounds of the invention gave the following results:

TABLE 1

| Compound of Example No. | Inhibition of PLA$_2$ (at 100 μM) | IC$_{50}$ (μM) |
|---|---|---|
| 1 | 100 | |
| 2 | 100 | 30 |
| 3 | 100 | |
| 4 | 100 | 6.8 |
| 5 | 11 | |
| 6 | 100 | |
| 7 | 94.4 | |
| 8 | 55.9 | |
| 9 | 100 | 8.5 |

The results show the compounds of the invention to have significant PLA$_2$ inhibitory activity in the assay in question.

EXAMPLE 12

The ability of the compounds of the invention to inhibit the lipoxygenase and/or cyclooxygenase pathways of arachidonic acid is examined in the in vivo arachidonic acid (AA)-/12-O-tetradecanoylphorbol acetate (TPA)-induced murine ear edema test.

According to this test, Swiss Webster female mice (Buckshire), approximately 8 weeks old, are placed into plastic boxes in groups of six. Eight groups of mice receive AA topically on the right ear, and another 8 groups receive TPA topically on the right ear. AA and TPA are dissolved in acetone at concentrations of 100 mg/ml ad 100 μg/ml respectively. The phlogistics are applied to the right ear by the means of an automatic pipet. Volumes of 10 μl are applied to the inner and outer surfaces of the ear. Each mouse receives either 2 mg/ear AA or 4 μg/ear TPA. The left ear (control) receives acetone delivered in the same manner. Oral and topical dosing regimens are as follows: (1) drugs are given 30 minutes prior to AA treatment, and (2) drugs are given 30 minutes after treatment with TPA.

Measurements are taken with Oditest calipers, 0-10 mm with 0.01 graduations. The right and left ears are measured after 1 hour AA-induced inflammation and 4 hours after TPA-induced inflammation.

The difference between right and left ear thickness is calculated and the significance is determined by a one way analysis of variance with Dunnett's comparisons to control (P=0.05). Drug effects are expressed as a percent change from control values:

% change from control =

$$\frac{(\text{Rt. ear} - \text{Lt. ear})\text{drug} - (\text{Rt. ear} - \text{Lt. ear})\text{control}}{(\text{Rt. ear} - \text{Lt. ear})\text{control}} \times 100$$

The results for the compounds of the invention are presented in Table 2.

TABLE 2

| Compound of Example No. | Mouse Ear Edema Assay % Change from Control | | ORAL |
|---|---|---|---|
| | TOPICAL | | |
| | AA[a] | TPA[a] | TPA[b] |
| 2 | −29 | −42 | |
| 4 | | −48 | −60 |
| 9 | | −55 | −25 |

[a] 1 mg/ear
[b] 100 mg/kg

The results show that the compounds of the invention tested demonstrate topical activity against AA- and TPA-induced mouse ear edema, evidencing an inhibitory effect on acute skin inflammation mediated by products of the lipoxygenase and/or cyclooxygenase pathway.

EXAMPLE 13

The ability of the compounds of the invention to inhibit both leukotriene and prostaglandin synthesis is examined in an assay which measures the ability of the compounds of the invention to inhibit the synthesis of arachidonic acid, PGE$_2$ and LTC$_4$ by murine peritoneal macrophages.

The assay is carried out as follows:

Macrophages are removed from the peritoneal cavity of 55-57 day old CD-1 mice (killed by CO$_2$ asphyxiation) by peritoneal lavage and centrifuged at 400×g for ten minutes. The cells are resuspended in Medium 199 and $4\times10^6$ cells are allowed to adhere on $35\times10$ mm Petri dishes for 1.5 hours at 37° C. in an atmosphere of 95% air and 5% $CO_2$. The cell monolayers are washed and incubated overnight in Medium 199 supplemented with 10% heat inactivated bovin serum containing 1 $\mu$Ci[$^{14}$C]-arachidonic acid, or in the absence of $^{14}$C-arachidonic acid when the supernatant is to be assayed by radioimmunoassay (RIA). The labeled cells are then washed and incubated at 37° C. for 2 hours in Medium 199 with the prostaglandin stimuli, zymosan, or 12-o-tetradecanoyl-phorbol-13-acetate (TPA) and in the presence or absence of test compounds. Following incubation, the supernatant is removed and subjected to radioimmunoassay in order to determine the percent inhibition of arachidonic acid, prostaglandin $E_2$ and leukotriene $C_4$ by the test compounds. The results in the assay for compounds of the invention are presented in Table 3.

TABLE 3

| Compound of Example No. | Mean % Inhibition ± S.E.* | | |
|---|---|---|---|
| | AA | PGE$_2$ | LTC$_4$ |
| 2 | 36.92 ± 6.29 | 81.18 ± 2.06 | 81.00 ± 1.79 |
| 4 | 34.12 ± 5.58 | 48.62 ± 9.32 | 91.95 ± 2.57 |

TABLE 3-continued

| Compound of Example No. | Mean % Inhibition ± S.E.* | | |
|---|---|---|---|
| | AA | PGE$_2$ | LTC$_4$ |
| 9 | 50.42 ± 2.50 | 73.50 ± 8.20 | 82.15 ± 2.48 |

*Compounds tested were used at a level of 10 $\mu$m.

The results show that the compounds tested have a significant inhibitory effect on the synthesis of AA, PGE$_2$ and LTC$_4$ by murine peritoneal macrophages, evidencing an inhibitory effect on PLA$_2$.

What is claimed is:

1. A compound having the formula

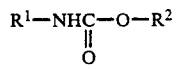

wherein
$R^1$ is alkyl of 8–22 carbon atoms;
$R^2$ is —(CH$_2$)$_n$NR$^4$R$^5$;
$R^4$ is hydrogen or lower alkyl;
$R^5$ is hydrogen or lower alkyl; and
n is 6–7.

2. The compound of claim 1, having the name dodecylcarbamic acid 6-(dimethylamino)hexyl ester.

3. The compound of claim 1, having the name hexadecylcarbamic acid 6-(dimethylamino)hexyl ester.

4. The compound having the name hexylcarbamic acid 6-(dimethylamino)hexyl ester.

* * * * *